United States Patent
Szapiro et al.

[11] Patent Number: 6,149,628
[45] Date of Patent: Nov. 21, 2000

[54] SYRINGE WITH TWO VARIABLE VOLUME CHAMBERS FOR CONTAINING AND ADMINISTERING MIXTURES OF PRODUCTS PROVIDED SEPARATELY

[76] Inventors: Jaime Luis Szapiro; Leonardo Szames; Saul Moreno, all of Tabaré 1641, Buenos Aires, Argentina

[21] Appl. No.: 09/344,974

[22] Filed: Jun. 28, 1999

[30] Foreign Application Priority Data

Jul. 20, 1998 [AR] Argentina .................. P 98 01 03536

[51] Int. Cl.⁷ .................................................. A61M 37/00
[52] U.S. Cl. ........................... 604/191; 604/89; 604/90
[58] Field of Search ........................ 604/191, 82, 89, 604/90, 91, 244, 245, 246, 187

[56] References Cited

U.S. PATENT DOCUMENTS

| | | | |
|---|---|---|---|
| 4,116,240 | 9/1978 | Guiney | 604/89 |
| 4,464,174 | 8/1984 | Ennis | 604/90 |
| 5,630,800 | 5/1997 | Blank et al. | 604/89 X |

*Primary Examiner*—John D. Yasko
*Attorney, Agent, or Firm*—Bachman & LaPointe, P.C.

[57] ABSTRACT

A syringe, of the type having two variable volume chambers inside the main cylindrical body, said chambers being separated by a displacing valve assembly, and being capable of housing components which should be mixed prior to injection. The novelty resides in the special conformation of parts and elements constituting said valve assembly, which comprises two cooperating, displacing elastomer portions; one of said portions being comprised by a peripheral, hollow cylindrical body bearing on the cylindrical wall of the main body, the other portion being an inner, solid cylindrical body slidingly bearing on the inner face of the front portion.

7 Claims, 10 Drawing Sheets

SYRINGE WITH TWO VARIABLE VOLUME CHAMBERS FOR CONTAINING AND ADMINISTERING MIXTURES OF PRODUCTS PROVIDED SEPARATELY

The instant invention relates to a syringe with two variable volume chambers for containing and administering mixtures of products provided separately, which is useful for administering products, such as some medicines comprised by two elements which are mixed previous to injecting them into a patient.

More particularly, the instant invention relates to a syringe capable of administering, indistinctly, two-component liquid products or dissolved powdered drugs. These syringes pertain to the group commercialized with the product to be injected contained therein, being capable of containing, separately, i.e. powder drug and its diluent, which are mixed at the time of injection. Therefore, it is included in the group of the so-called "pre-filled syringes", since they are provided with the medicine incorporated therein, so that the user has no contact with the drug.

PRIOR ART

Several syringes are known serving for the above purposes; all of them have a main cylindrical hollow body inside which the medicine is contained and through which a coaxial plunger displaces. In all cases, the lower base of said cylindrical main body is open and allows displacement of said plunger. To this end, these syringes include a flange projecting outwardly which serves as a bearing point for the user to push or pull from said plunger. On the other hand, the opposite base of said main cylindrical body defines a hollow and coaxial frustoconical spout, acting as a plugging or coupling means for fixing the injection needle. See Argentine patent No. 239,763 of the owners of the present invention.

Double chamber pre-filled syringes are already known. They may be used for medicines comprised by two ingredients, or when powdered drug is placed into one of the chambers and the diluent into the adjacent chamber. In all cases, a first displacement of the plunger takes place in order to mix the products, and a second displacement of the plunger is made for injecting the contents already mixed. Thus, two tight and adjacent chambers are defined inside said main body, the chambers being separated by valve means which, when the plunger displaces, allows communication between the chambers for dilution and/or mixing of the components and also outlet of the product through the injection needle.

The owners of the instant application have already obtained Argentine patent No. 247,101 "Double chamber disposable syringe for administering indistinctly liquid products or diluted powder drugs", wherein the open lower base of the main cylindrical body is closed by an elastomer plug which includes a central conduit through which the syringe plunger passes; while the active head of said plunger is also an elastomer plug which, forming part of said plunger, has its peripheral edge seated on the inner cylindrical surface of the main body and acts as a valve resource dividing the interior of said main body into two inner variable volume chambers. When said active head displaces opposite to the injection direction, allows communication between said two inner chambers, thus allowing mixing of the products contained therein; in turn, when the head displaces in the injection direction, it causes exit of the diluted or mixed product towards the needle.

Although results obtained are very satisfactory, construction is delicate, requires high precision and its cost is relatively high, being a disposable product.

The owners of the instant invention have also obtained Argentine patent No. 332787, "Disposable syringe with two variable volume chambers" wherein operation of the plunger active head as sliding elastomer plug is improved. Such head is housed into the inner cavity of an elastomer head bearing on the inner cylindrical wall of the main body, thus forming a double seat valve closure means. In this case, the novel feature is that passage of the products is produced centrally, through the valve body and not through the periphery thereof.

This case, as well as the previous one, has given satisfactory results, but also requires high precision in the construction that increases the cost of the assembly.

U.S. Pat. No. 4,613,326, to Joseph M. Szwarc also discloses an injection syringe with variable volume double chamber for obtaining mixture of two components immediately before injection. In this case, the active head of plunger 38 also includes an elastomer plug 36 defining the inner closure of a variable volume chamber and acting in coordination with another sliding plug 31 which is the closure of the other variable volume chamber communicating to the outlet towards the injection needle. To attain communication between the two chambers, a novel "bypass" is incorporated, which comprises an inner cavity 34 adjacent said outlet chamber.

This novel solution has the disadvantage that, invariably, the construction of special main cylindrical bodies is required, such bodies being capable of actuation only with the resources and means disclosed and shown in said patent.

MAIN OBJECT OF THE INVENTION

The syringe of the instant invention is also a double chamber syringe, capable of producing mixture of the two components by means of plunger displacement, the novelty residing in that the inner valve means used does not require any modification in the main cylindrical body of the syringe or inclusion of special plugs closing the open base thereof and allowing the plunger passage without undesirable losses of the contents.

The instant invention is a novel constructive solution adapting itself to any conventional syringe, made of glass or plastics, without modification at all in its main body.

In this case, the use of a particular inner valve means, housed inside the main cylindrical body divides it into two inner variable volume chamber, while the active plunger head is in turn a closure stop for the distal chamber.

Such inner valve means comprises two elastomer portions operating in mutual cooperation, allowing mixing of the components when the plunger displaces in a direction contrary to the injection action and causing outlet of the mixture towards the injection needle when such plunger displaces towards the injection needle, i.e. in the direction of the injection action.

The main advantage is that passage of the components during the mixing action and also during injection is not effected through the periphery of the inner valve assembly. Therefore, the closure adjustment of this valve assembly on the inner cylindrical wall of the main body is simpler and safer.

Another advantage is that both elastomer portions forming said valve assembly are easy to construct and the cost is low, being useful in any conventional syringe. Therefore, the manufacturer has the possibility of producing such syringes for conventional use, with a single inner chamber, or incorporate this valve assembly so that the same syringe be used as a double chamber device housing two products which are separated until the injection time.

The main object of the invention is a syringe with two variable volume chambers for administering product mixtures which are provided separately, said chambers being located inside the main cylindrical body, separated by a valve assembly comprising two elastomer portions, cooperating therebetween, i.e.: a peripheral portion which is a cylindrical and hollow body having one of its bases wholly open, and the other base includes a central conduit, while its outer cylindrical surface has at least two annular projecting flanges bearing on the inner surface of said main cylindrical body of the syringe; while the other inner portion is a rigid cylindrical body having an upper central cylindrical projection which is coaxially and slidingly housed inside the central conduit of the first portion and has on the outer cylindrical surface, at least two annular projecting flanges bearing on the inner cylindrical surface of said first portion.

One of said two valve portions of cooperating action includes at least a cavity mating with the facing cylindrical surfaces, thus creating a communication allowing fluid passage therethrough and through the central conduit of the peripheral portion.

A constructive alternative, within the definition of the previous paragraph, is that said communication cavity be defined mating with the outer cylindrical surface of the inner solid valve portion. Several communication cavities made on said surface, orderly distributed, are also contemplated within the scope of the invention.

Another alternative, also within the definition above, is that the communication cavity be defined mating with the inner cylindrical surface of the peripheral and hollow valve portion. Also several communication cavities, evenly distributed, may be practiced in said surface.

BRIEF DESCRIPTION OF THE DRAWINGS

A preferred embodiment of the invention will be now described in connection with the accompanying drawings, in which.

In all figures the same reference numerals correspond to the same or equivalent parts constituting the assembly, according to the example selected for explaining the syringe of the invention.

DETAILED DESCRIPTION OF THE PREFERRED EMBODIMENT

As may be seen in the figures, the syringe of the invention is comprised by a main body 1 which is a straight axis circular cylinder; the lower base 2 is open and includes the conventional cantilever annular flange 3 employed by the user as a support for acting plunger 10. The upper base 4 includes an injection coaxial hollow spout 5, which may be closed by a closure plug 6 (which avoids the contact of the liquid with the outside and the needle) which, along with annular flange 7 define a coupling means for placing the plugging cone 8 protecting the injection needle 9.

Figure 1:
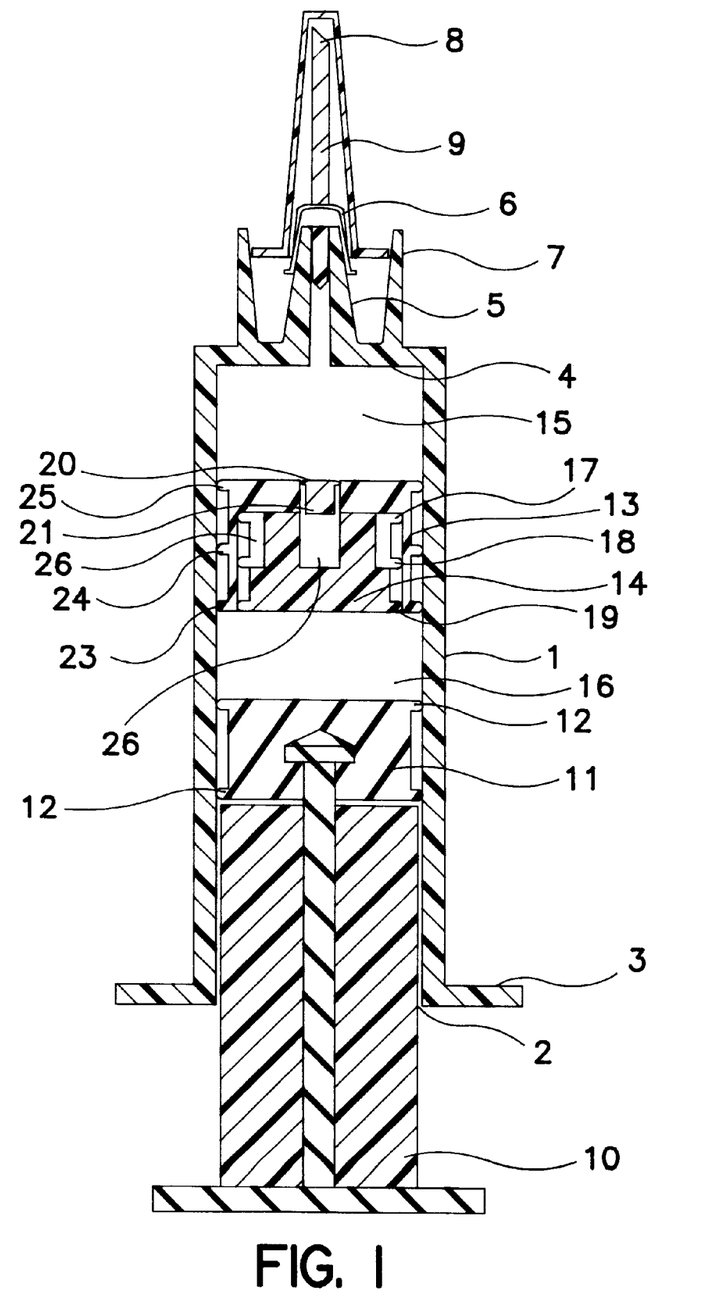
FIG. 1 is a longitudinal section showing a double chamber syringe of the present invention.
Figure 2:
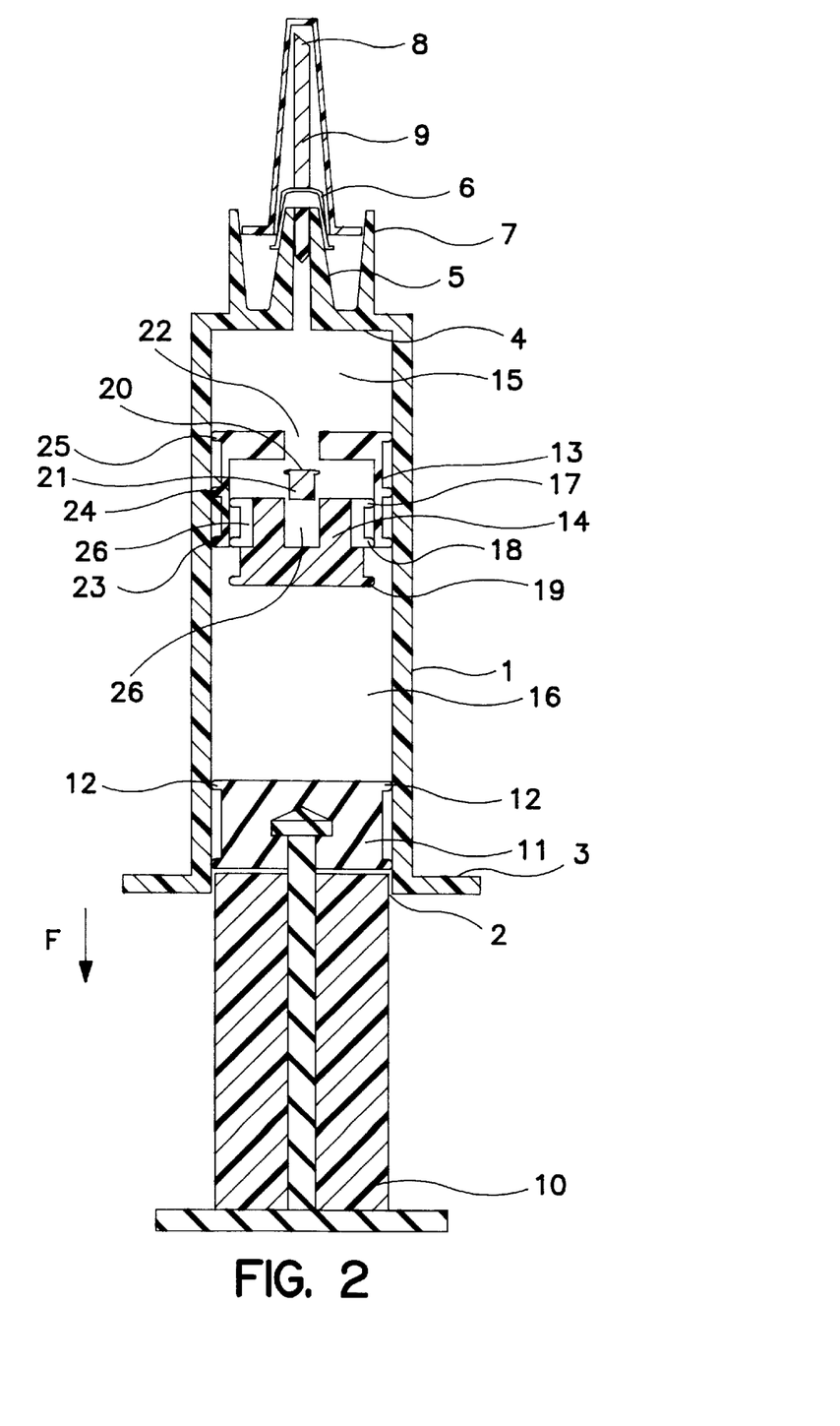
FIG. 2 is a longitudinal section of the syringe of FIG. 1 showing the arrangement of elements and parts upon mixing of the components to be injected.
Figure 3:
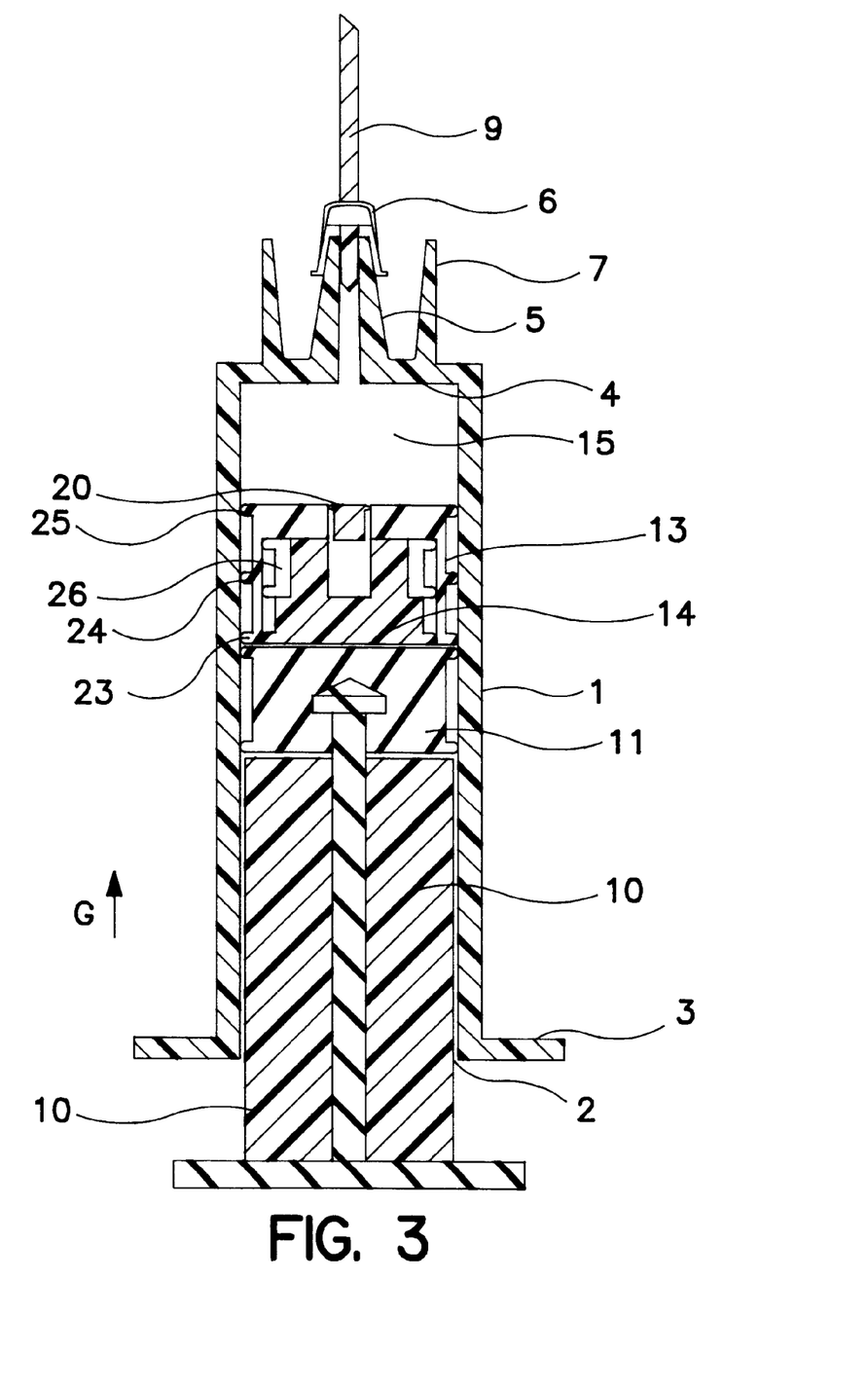
FIG. 3 is a longitudinal section of the syringe of former figures showing the arrangement of elements and parts during injection of the mixture obtained.
Figure 4:
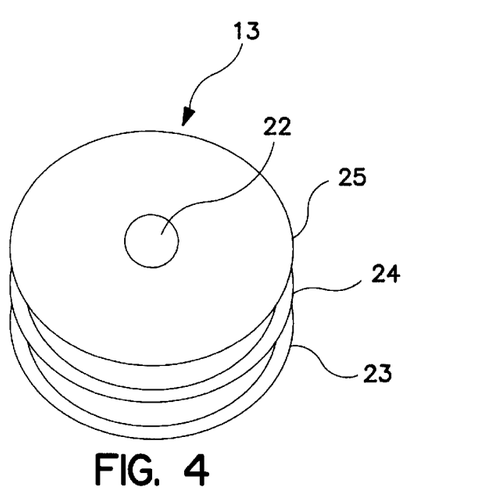
FIG. 4 is an elevation perspective view from the upper base of the peripheral hollow valve portion of the valve assembly of the syringe of the invention.

As may be seen in the three first figures, plunger 10 has an active head 11 acting as a sliding closure plug preventing outlet of liquid from the interior of the main cylindrical body 1 through said open base 2 of such body. To this end, said head 11 is made of elastomer and has annular flanges 12 bearing on the inner cylindrical surface of body 1 for providing tightness to such closure, further allowing the normal sliding of the plunger without undesired liquid losses.

The novelty of the invention resides in the special inner valve assembly formed by the peripheral, hollow valve portion 13 and the rigid inner valve portion 14. This assembly divides the interior of the main cylindrical body 1 into two variable volume chambers 15 and 16, which will be called proximal chamber 15 limited by said valve assembly and the base 4 of the main body, and distal chamber 16 limited by the valve assembly and the open base 2 of said main body 1.

Figure 8:
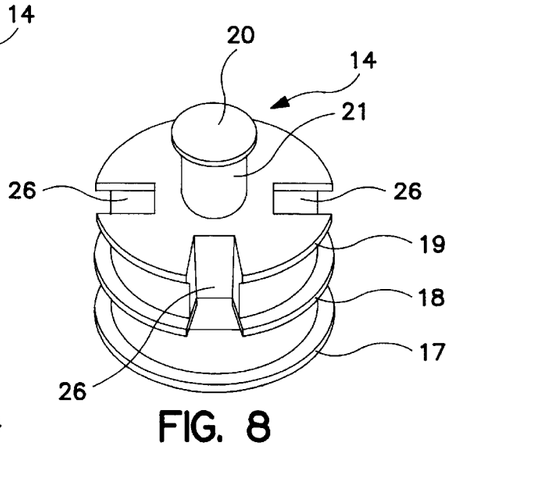
FIG. 8 is a perspective view showing the rigid inner valve portion of the valve assembly of the double chamber syringe of the invention.
Figure 9:
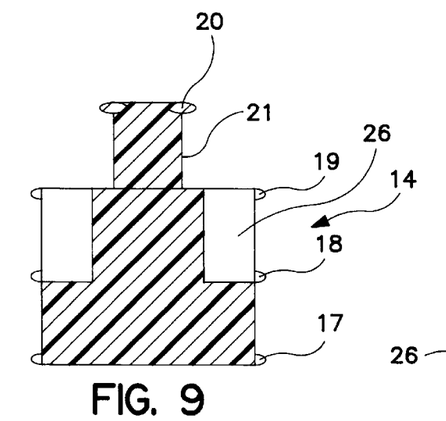
FIG. 9 is a vertical section showing the same rigid inner valve portion of the valve assembly of the double chamber syringe of the invention.
Figure 10:
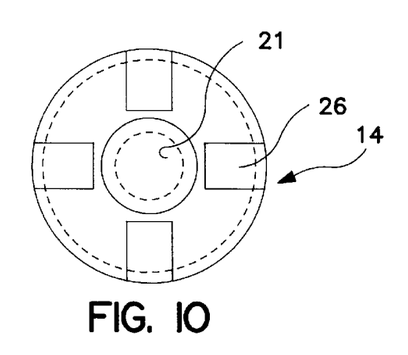
FIG. 10 is a top plan view showing the same rigid, inner valve portion of FIG. 8 of the valve assembly of the double chamber syringe of the invention.

As already known, said variable volume chambers 15 and 16 are of the kind used for housing two products separately, said products being mixed before the injection. In this regard, FIG. 1 shows the way in which said valve assembly 13, 14 maintains said chambers isolated one from the other; while FIG. 2 shows operation of these inner valve elements when the user displaces plunger 10 in a direction opposite to that of injection, indicated by arrow F; while FIG. 3 shows the way in which said valve elements operate when plunger 10 is displaced in the direction of injection, such as shown by arrow G. In fact, specially as seen in FIGS. 8, 9 and 10, the inner, solid valve portion 14, as well as its coaxial projecting portion 21, have annular flanges 17, 18, 19 and 20, three of which bear on the inner cylindrical surface of the peripheral portion, while the fourths flange 20 bears on the walls of the communication conduit 22 of valve portion 13.

In turn, this valve portion 13, apart from said communication conduit 22, has also annular flanges 23, 24 and 25 which, in this case, bear on the inner cylindrical surface of cylindrical body 1.

Turning to FIG. 2, when plunger 10 is displaced in the direction F, a depression is generated at the distal chamber 16 which causes the relative displacement of portion 14 relative to portion 13 and, consequently, passage of the liquid component housed in the proximal chamber 15 which enters, through the communication conduit 22 and after passing through transference cavities 26, towards the distal chamber 16 wherein the other component is located, thus producing mixture of both products.

With head 11 of plunger 10 housed in the position shown in FIG. 2, the user may stir the syringe until the proper mixture of the components is obtained.

Displacing plunger 10 in direction G, the first effect is that the mixture of the two components travels opposite to the direction indicated in the previous paragraph, passes first through transference cavities 26 and then, through conduit 22, enters into the proximal chamber 15.

Once the whole mixture is displaced to the proximal chamber 15, head 11 of plunger 10 pushes the solid portion 14 until the closure position shown in FIG. 3 is attained, i.e. blocking the communication conduit 22, the syringe being thus in condition of producing injection of the mixture through needle 9, merely removing the protecting sheath 8, and then continuing pushing the plunger 10 in the direction of injection G, since plug 6 displaces thus allowing outlet of liquid through the injection needle.

Figure 5:
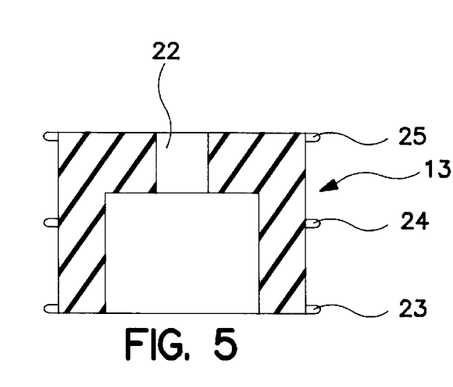
FIG. 5 is a vertical section showing the same peripheral, hollow valve portion of the inner valve assembly of the double chamber syringe of the invention.
Figure 6:
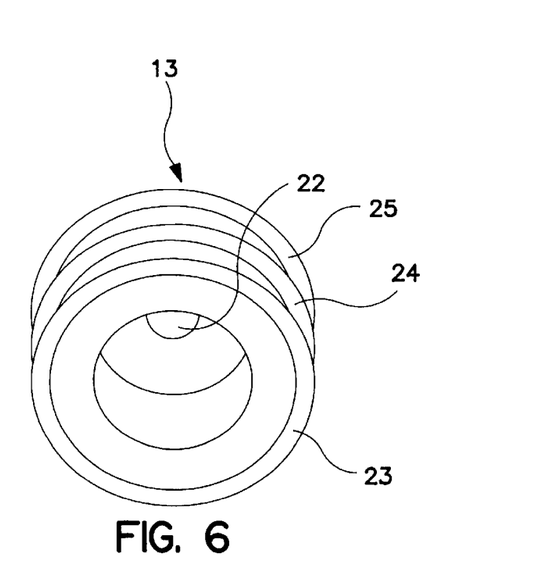
FIG. 6 is an elevation perspective view from the lower base of the peripheral hollow valve portion of the valve assembly of the syringe of the invention.
Figure 7:
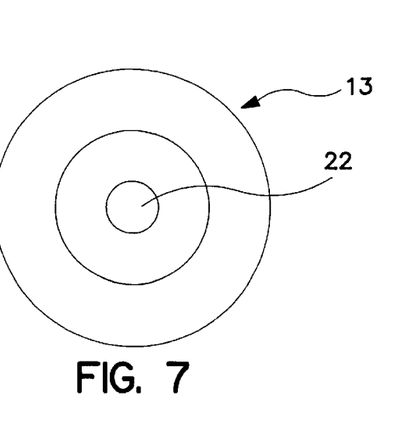
FIG. 7 is a lower plan view of the same peripheral valve portion of the valve assembly of the double chamber syringe of the invention.

FIGS. 5 and 6 clearly show the inner, solid valve portion 14 of the valve assembly. The example described till now is that shown in FIG. 5, wherein the solid portion has a plurality of transference cavities 26; however, in some cases, a single transference cavity will suffice to obtain the desired transference.

A characteristic of the invention is that said transference cavities 26 are always located in the solid portion 14 and on tightening flanges 17 and 18.

Figure 11:
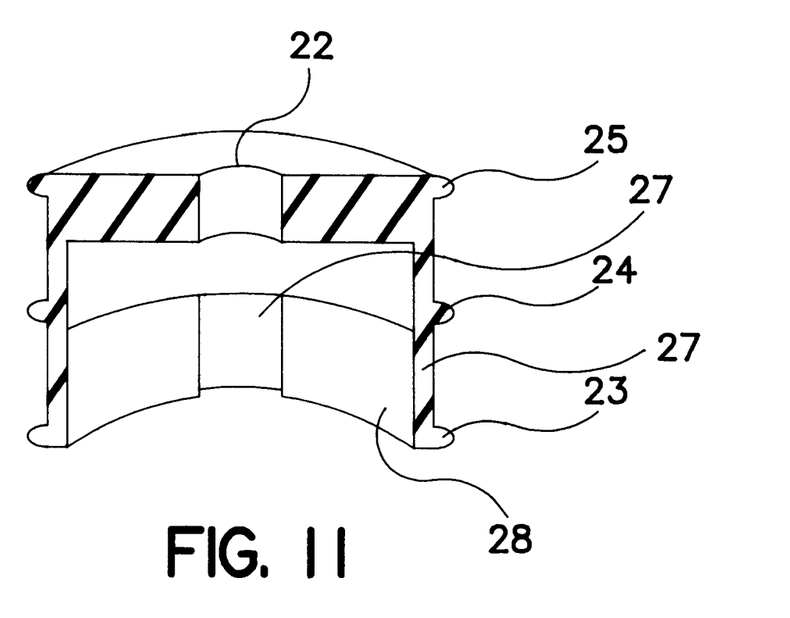
FIG. 11 is a perspective view of the peripheral, hollow valve portion in an alternative embodiment, shown along a vertical plane.
Figure 12:
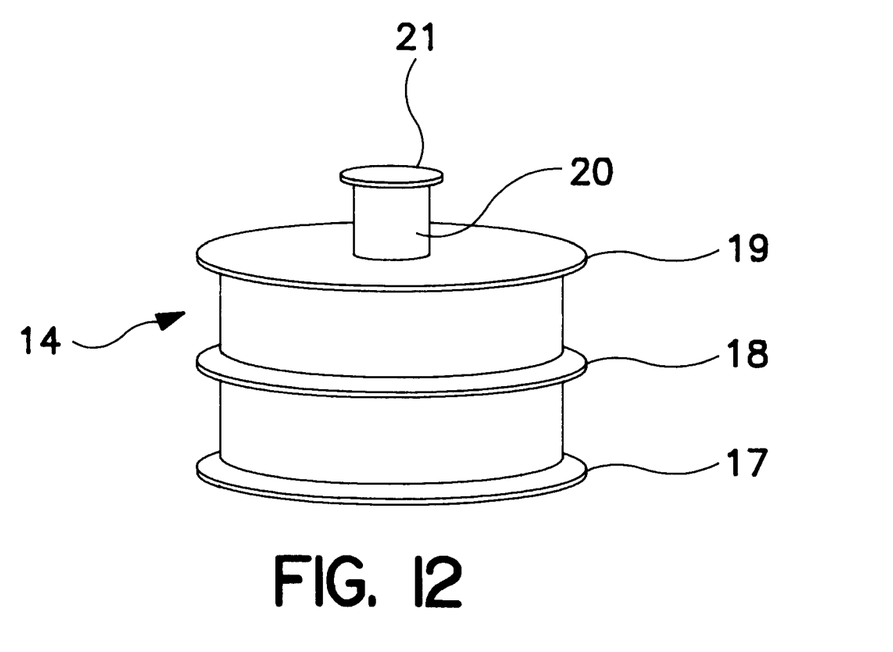
FIG. 12 is a perspective view showing the inner, rigid valve portion according to a constructive alternative intended for acting with the portion shown in the former figure.
Figure 13:
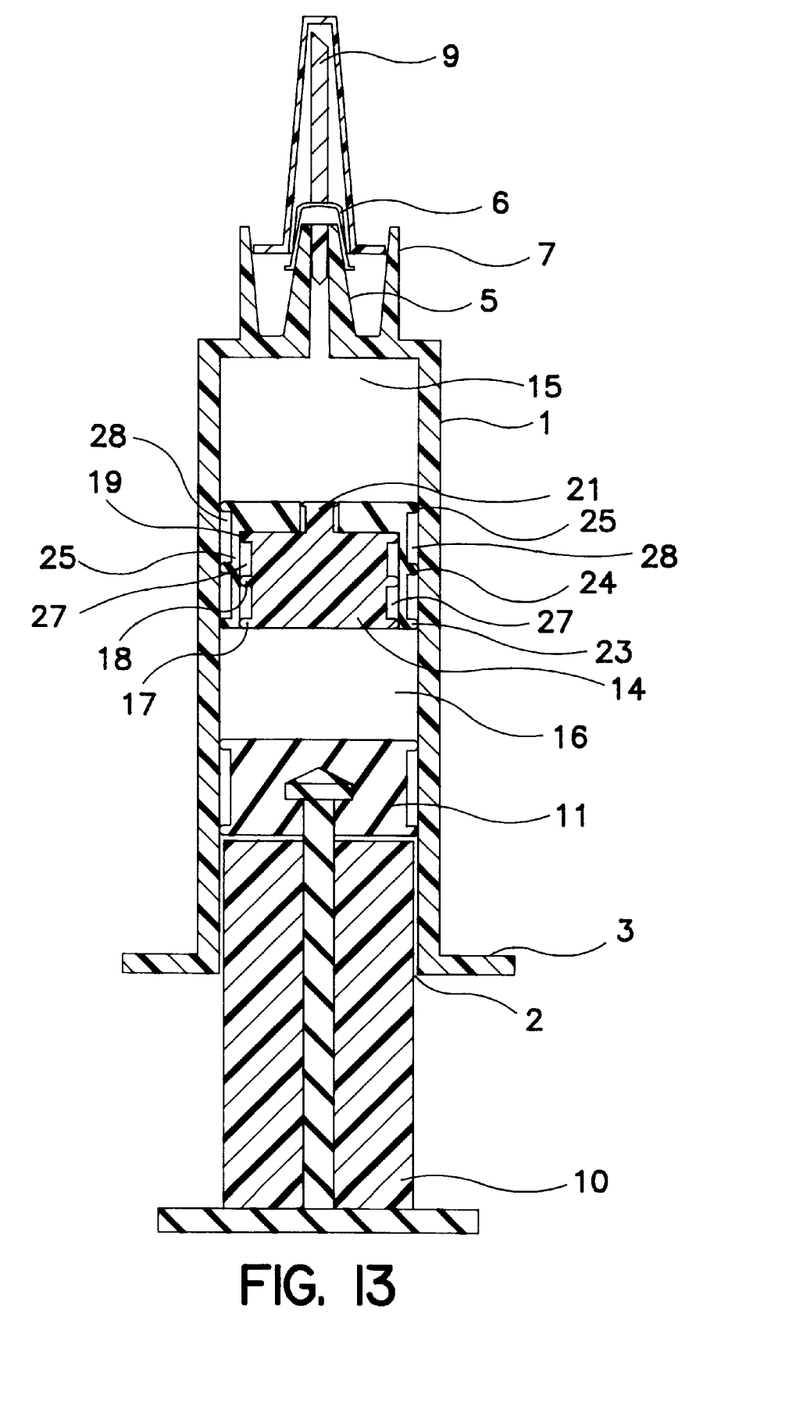
FIG. 13 is a longitudinal section showing a double chamber syringe, the valve assembly of which includes the constructive alternatives shown in FIGS. 11 and 12.

FIGS. 11, 12 and 13 show that the inner valve assembly may carry out the function explained, with a constructive modification, which should be considered within the scope of the invention, being an equivalent resource. In this case, the hollow peripheral portion 13 has at least a cavity 27 in the inner face 28. It is clear that such cavity 27 acts as a transference communication, allowing fluid passage from and towards conduit 22 when the solid portion 14 is displaced towards the distal chamber 16. In this case, it is not required that solid portion 14 be provided with said cavities 26.

According to the invention, when the solid portion 14 is in the closure position, housed inside the hollow portion 13, said cavity 27 is at a level lower to that of tightening flange 19.

FIG. 11 shows the alternative of including a plurality of cavities 27, under the same constructive conditions as above, this alternative being foreseen for optimizing the valve operation in some cases of more viscous mixtures.

Figure 14:
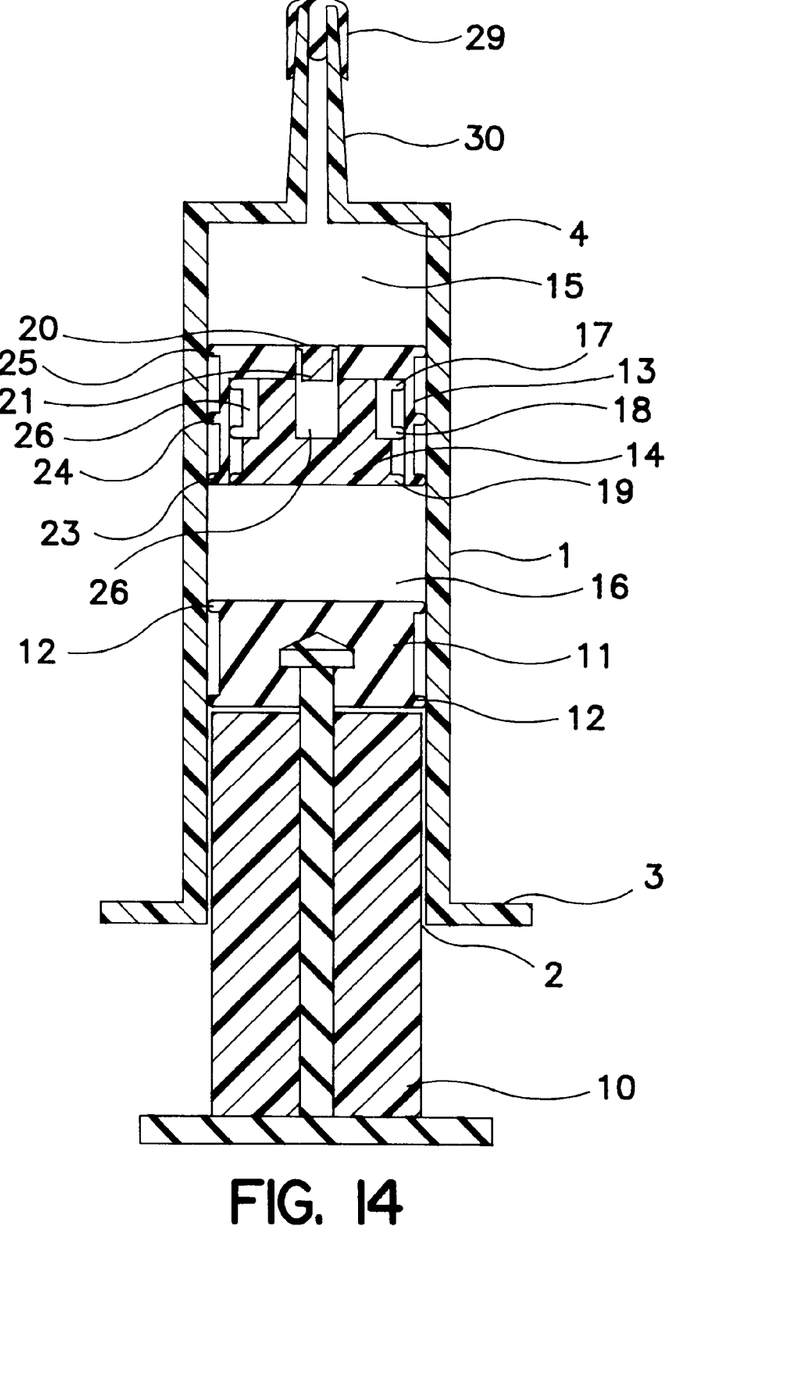
FIGS. 14, 15 and 16 are cross sections showing a conventional syringe converted in a double chamber syringe by the addition of the valve assembly of the invention.
Figure 15:
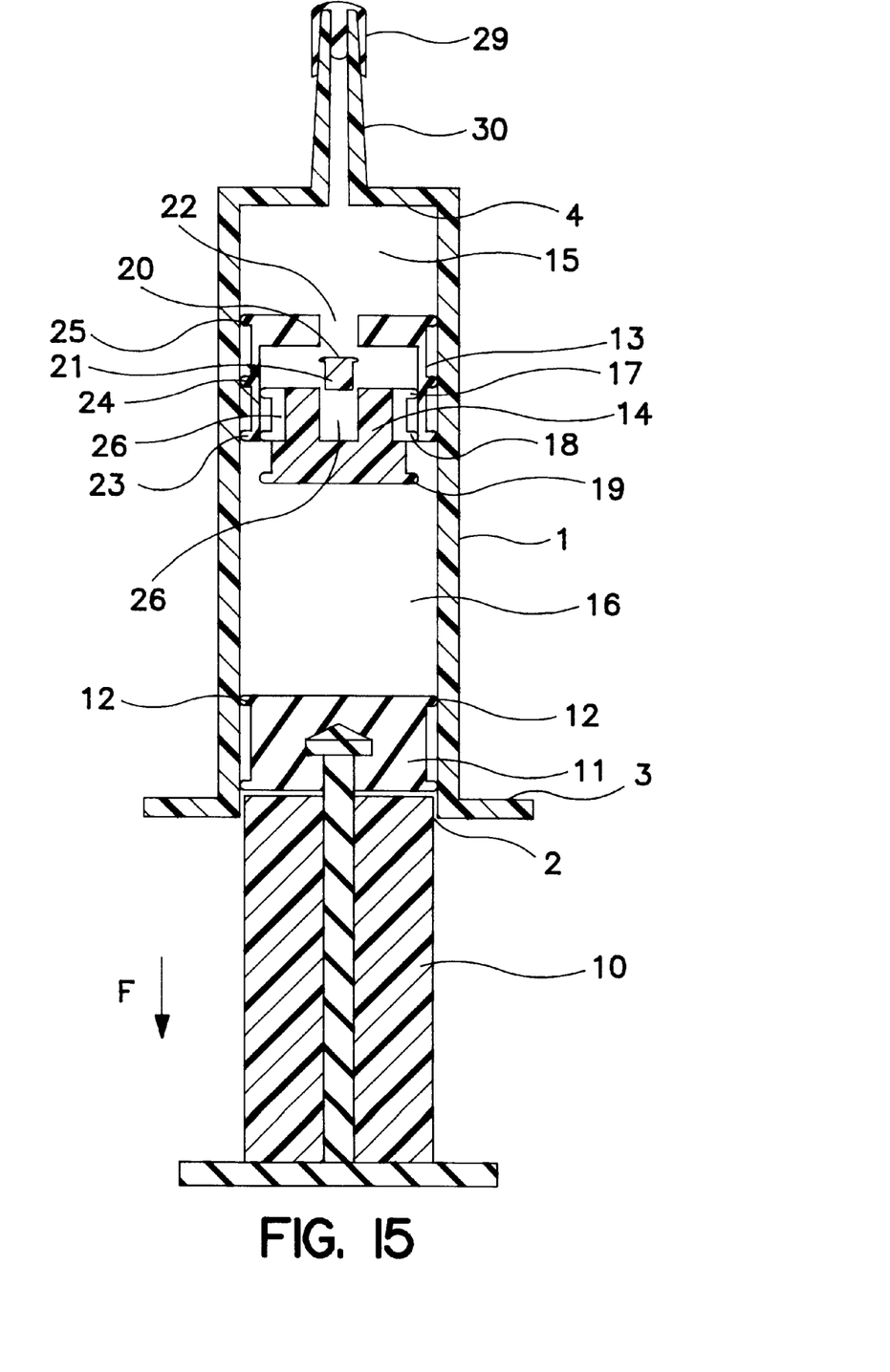
Figure 16:
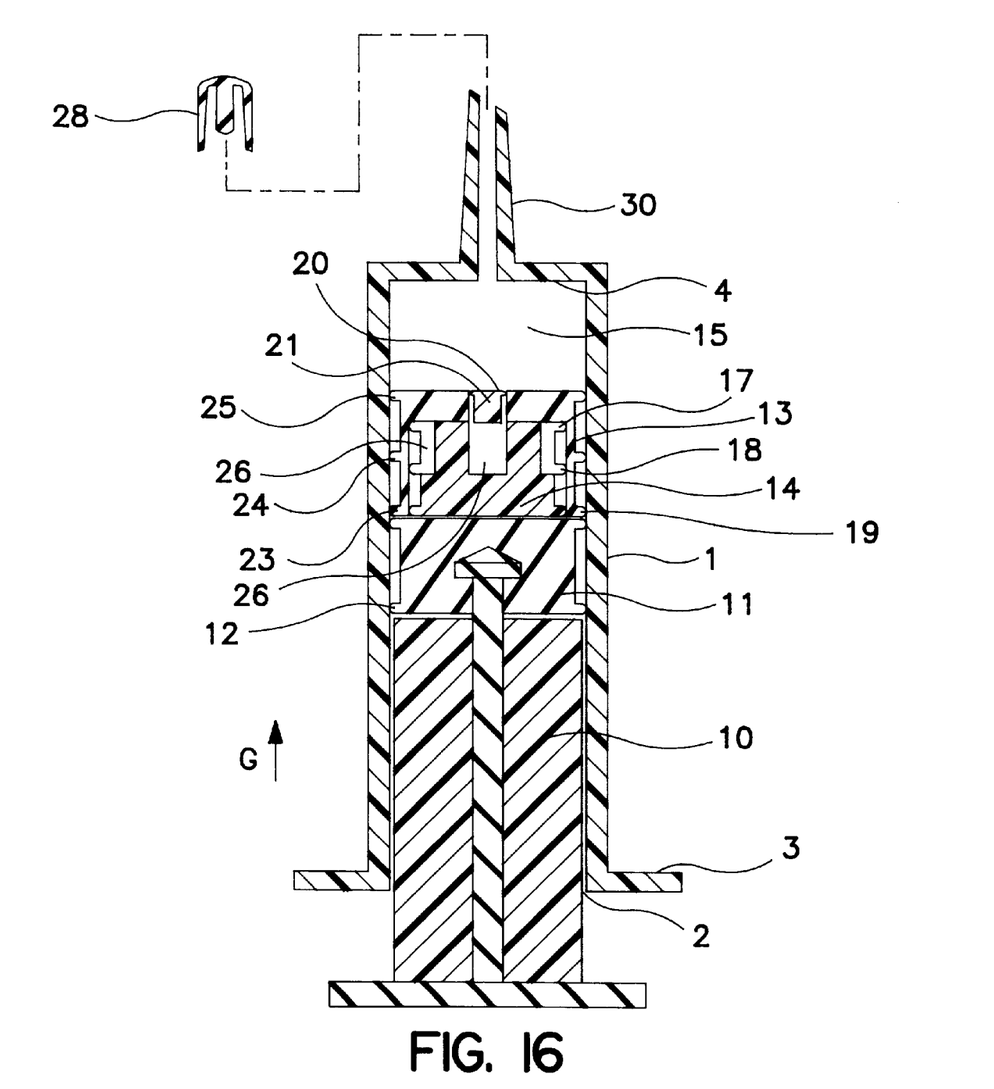

Further, FIGS. 14, 15 and 16 show that the same valve means may be used in conventional syringes and in those syringes that, due to their shape, do not admit coupling of the needle, for avoiding direct injection, the plugging cone 30 of which is blocked by an upper plug 29. Said plug should be merely hand removed, the needle placed and the spout (of special shape) introduced into one of the tubes of a diluent serum bag, then proceeding with injection of the mixture. It is to be noted that the valve assembly may be installed through the open base 2 of the syringe body without requiring any modification.

What is claimed is:

1. A syringe for containing, mixing and administering two elements of a medicament comprises: a main body having a sidewall defining a chamber; moveable valve means dividing the chamber into a proximal variable volume chamber and a distal variable volume chamber; medicament outlet communicating with the proximate variable volume chamber; a plunger reciprocally movable in the distal variable volume chamber in a first direction and a second direction; the moveable valve means comprises (1) a hollow peripheral valve portion sealingly located on the sidewall of the chamber and (2) a rigid inner valve portion movably received in the hollow peripheral valve portion and moveable between a first position for establishing communication between the proximal and distal variable volume chambers and a second position for prohibiting communication between said proximal and distal variable volume chambers, wherein movement of the plunger in the first direction moves the inner rigid valve portion to the first position for mixing the two elements in the distal variable volume chamber and movement of the plunger in the second direction transfers the mixed two elements from the distal variable volume chamber to the proximal variable volume chamber until the plunger abuts the inner rigid valve portion and moves same to the second position upon continued movement of the plunger in the second direction for administering the medicament through the medicament outlet.

2. A syringe according to claim 1, wherein the hollow valve portion is cup-shaped and has a sidewall portion extending from a base portion, the base portion includes a control conduit.

3. A syringe according to claim 2, wherein the inner rigid valve portion has a body portion sealingly received on the sidewall portion on the hollow valve portion and a projecting portion received in the central conduit of the hollow valve portion when in the second position.

4. A syringe according to claim 3, wherein a portion of the body portion is provided with at least one transfer cavity wherein the projecting portion is removed from the central conduit for establishing communication between the second conduit and the transfer cavities when in the first position.

5. A syringe according to claim 3, wherein a portion of the sidewall portion is provided with at least one transfer cavity wherein the projecting portion is removed from the central conduit for establishing communication between the second conduit and the transfer cavities when in the first position.

6. A syringe according to claim 1, wherein the hollow peripheral valve portions have a plurality of flanges for sealing on the sidewall of the chamber.

7. A syringe according to claim 3, wherein the body portion has a plurality of flanges for sealing on the sidewall portion of the hollow valve portion.

* * * * *